(12) United States Patent
Nath et al.

(10) Patent No.: US 8,173,612 B2
(45) Date of Patent: May 8, 2012

(54) CHEMOTHERAPY INVOLVING ANTISENSE OLIGONUCLEOTIDES FOR PREVENTING AND/OR TREATING PULMONARY FIBROSIS

(76) Inventors: Rahul K. Nath, Houston, TX (US); Usha Nath, Houston, TX (US)

( * ) Notice: Subject to any disclaimer, the term of this patent is extended or adjusted under 35 U.S.C. 154(b) by 1636 days.

(21) Appl. No.: 11/521,843

(22) Filed: Sep. 15, 2006

(65) Prior Publication Data

US 2011/0172162 A1    Jul. 14, 2011

Related U.S. Application Data

(63) Continuation-in-part of application No. 11/021,603, filed on Dec. 21, 2004, now Pat. No. 7,396,823, which is a continuation-in-part of application No. 10/149,352, filed on Jun. 10, 2002, now Pat. No. 7,173,122.

(30) Foreign Application Priority Data

Dec. 15, 1999 (GB) .................................... 9929487.8
Dec. 12, 2000 (WO) ...................... PCT/GB00/04741

(51) Int. Cl.
*A61K 31/70* (2006.01)
*C07H 21/02* (2006.01)
*C07H 21/04* (2006.01)
*C12Q 1/68* (2006.01)

(52) U.S. Cl. ...... 514/44 A; 435/375; 435/377; 536/23.1; 536/24.1; 536/24.5

(58) Field of Classification Search ........................ None
See application file for complete search history.

*Primary Examiner* — Sean McGarry
(74) *Attorney, Agent, or Firm* — The Matthews Firm

(57) ABSTRACT

The invention provides, in the treatment of malignant tumors, antisense DNA oligonucleotides which are effective in inhibiting the expression of a wild type COL1A1 gene, in combination with a chemotherapy drug, typically bleomycin, cyclophosphamide, or methotrexate, which otherwise is known to cause lung disease such as pulmonary fibrosis.

23 Claims, No Drawings

SEQUENCE LISTING

```
<160> NUMBER OF SEQ ID NOS: 14

<210> SEQ ID NO 1
<211> LENGTH: 6728
<212> TYPE: DNA
<213> ORGANISM: Homo sapiens
<220> FEATURE:
<221> NAME/KEY: CDS
<222> LOCATION: (120)..(4511)
<220> FEATURE:
<221> NAME/KEY: sig_peptide
<222> LOCATION: (120)..(185)

<400> SEQUENCE: 1
agcagacggg agtttctcct cggggtcgga gcaggaggca cgcggagtgt gaggccacgc        60
atgagcggac gctaacccccc tccccagcca caaagagtct acatgtctag ggtctagac      119 atg ttc agc ttt gtg gac ctc cgg ctc ctg ctc ctc tta gcg gcc acc       167
Met Phe Ser Phe Val Asp Leu Arg Leu Leu Leu Leu Leu Ala Ala Thr
  1               5                  10                  15 gcc ctc ctg acg cac ggc caa gag gaa ggc caa gtc gag ggc caa gac       215
Ala Leu Leu Thr His Gly Gln Glu Glu Gly Gln Val Glu Gly Gln Asp
             20                  25                  30 gaa gac atc cca cca atc acc tgc gta cag aac ggc ctc agg tac cat       263
Glu Asp Ile Pro Pro Ile Thr Cys Val Gln Asn Gly Leu Arg Tyr His
         35                  40                  45 gac cga gac gtg tgg aaa ccc gag ccc tgc cgg atc tgc gtc tgc gac       311
Asp Arg Asp Val Trp Lys Pro Glu Pro Cys Arg Ile Cys Val Cys Asp
     50                  55                  60 aac ggc aag gtg ttg tgc gat gac gtg atc tgt gac gag acc aag aac       359
Asn Gly Lys Val Leu Cys Asp Asp Val Ile Cys Asp Glu Thr Lys Asn
 65                  70                  75                  80 tgc ccc ggc gcc gaa gtc ccc gag ggc gag tgc tgt ccc gtc tgc ccc       407
Cys Pro Gly Ala Glu Val Pro Glu Gly Glu Cys Cys Pro Val Cys Pro
                 85                  90                  95 gac ggc tca gag tca ccc acc gac caa gaa acc acc ggc gtc gag gga       455
Asp Gly Ser Glu Ser Pro Thr Asp Gln Glu Thr Thr Gly Val Glu Gly
            100                 105                 110 ccc aag gga gac act ggc ccc cga ggc cca agg gga ccc gca ggc ccc       503
Pro Lys Gly Asp Thr Gly Pro Arg Gly Pro Arg Gly Pro Ala Gly Pro
        115                 120                 125 cct ggc cga gat ggc atc cct gga cag cct gga ctt ccc gga ccc ccc       551
Pro Gly Arg Asp Gly Ile Pro Gly Gln Pro Gly Leu Pro Gly Pro Pro
    130                 135                 140 gga ccc ccc gga cct ccc gga ccc cct ggc ctc gga gga aac ttt gct       599
Gly Pro Pro Gly Pro Pro Gly Pro Pro Gly Leu Gly Gly Asn Phe Ala
145                 150                 155                 160 ccc cag ctg tct tat ggc tat gat gag aaa tca acc gga gga att tcc       647
```

-continued

| | | |
|---|---|---|
| Pro Gln Leu Ser Tyr Gly Tyr Asp Glu Lys Ser Thr Gly Gly Ile Ser<br>                165                        170                     175 | | |
| gtg cct ggc ccc atg ggt ccc tct ggt cct cgt ggt ctc cct ggc ccc<br>Val Pro Gly Pro Met Gly Pro Ser Gly Pro Arg Gly Leu Pro Gly Pro<br>               180                      185                     190 | 695 | |
| cct ggt gca cct ggt ccc caa ggc ttc caa ggt ccc cct ggt gag cct<br>Pro Gly Ala Pro Gly Pro Gln Gly Phe Gln Gly Pro Pro Gly Glu Pro<br>        195                     200                     205 | 743 | |
| ggc gag cct gga gct tca ggt ccc atg ggt ccc cga ggt ccc cca ggt<br>Gly Glu Pro Gly Ala Ser Gly Pro Met Gly Pro Arg Gly Pro Pro Gly<br> 210                  215                     220 | 791 | |
| ccc cct gga aag aat gga gat gat ggg gaa gct gga aaa cct ggt cgt<br>Pro Pro Gly Lys Asn Gly Asp Asp Gly Glu Ala Gly Lys Pro Gly Arg<br>225                  230                     235                   240 | 839 | |
| cct ggt gag cgt ggg cct cct ggg cct cag ggt gct cga gga ttg ccc<br>Pro Gly Glu Arg Gly Pro Pro Gly Pro Gln Gly Ala Arg Gly Leu Pro<br>               245                     250                     255 | 887 | |
| gga aca gct ggc ctc cct gga atg aag gga cac aga ggt ttc agt ggt<br>Gly Thr Ala Gly Leu Pro Gly Met Lys Gly His Arg Gly Phe Ser Gly<br>         260                     265                     270 | 935 | |
| ttg gat ggt gcc aag gga gat gct ggt cct gct ggt cct aag ggt gag<br>Leu Asp Gly Ala Lys Gly Asp Ala Gly Pro Ala Gly Pro Lys Gly Glu<br>             275                     280                     285 | 983 | |
| cct ggc agc cct ggt gaa aat gga gct cct ggt cag atg ggc ccc cgt<br>Pro Gly Ser Pro Gly Glu Asn Gly Ala Pro Gly Gln Met Gly Pro Arg<br> 290                  295                     300 | 1031 | |
| ggc ctg cct ggt gag aga ggt cgc cct gga gcc cct ggc cct gct ggt<br>Gly Leu Pro Gly Glu Arg Gly Arg Pro Gly Ala Pro Gly Pro Ala Gly<br>305                  310                     315                   320 | 1079 | |
| gct cgt gga aat gat ggt gct act ggt gct gcc ggg ccc cct ggt ccc<br>Ala Arg Gly Asn Asp Gly Ala Thr Gly Ala Ala Gly Pro Pro Gly Pro<br>               325                     330                     335 | 1127 | |
| acc ggc ccc gct ggt cct cct ggc ttc cct ggt gct gtt ggt gct aag<br>Thr Gly Pro Ala Gly Pro Pro Gly Phe Pro Gly Ala Val Gly Ala Lys<br>            340                     345                     350 | 1175 | |
| ggt gaa gct ggt ccc caa ggg ccc cga ggc tct gaa ggt ccc cag ggt<br>Gly Glu Ala Gly Pro Gln Gly Pro Arg Gly Ser Glu Gly Pro Gln Gly<br>         355                     360                     365 | 1223 | |
| gtg cgt ggt gag cct ggc ccc cct ggc cct gct ggt gct gct ggc cct<br>Val Arg Gly Glu Pro Gly Pro Pro Gly Pro Ala Gly Ala Ala Gly Pro<br>370                  375                     380 | 1271 | |
| gct gga aac cct ggt gct gat gga cag cct ggt gct aaa ggt gcc aat<br>Ala Gly Asn Pro Gly Ala Asp Gly Gln Pro Gly Ala Lys Gly Ala Asn<br>385                  390                     395                   400 | 1319 | |
| ggt gct cct ggt att gct ggt gct cct ggc ttc cct ggt gcc cga ggc<br>Gly Ala Pro Gly Ile Ala Gly Ala Pro Gly Phe Pro Gly Ala Arg Gly<br>               405                     410                     415 | 1367 | |
| ccc tct gga ccc cag ggc ccc ggc ggc cct cct ggt ccc aag ggt aac<br>Pro Ser Gly Pro Gln Gly Pro Gly Gly Pro Pro Gly Pro Lys Gly Asn<br>            420                     425                     430 | 1415 | |
| agc ggt gaa cct ggt gct cct ggc agc aaa gga gac act ggt gct aag<br>Ser Gly Glu Pro Gly Ala Pro Gly Ser Lys Gly Asp Thr Gly Ala Lys<br>         435                     440                     445 | 1463 | |
| gga gag cct ggc cct gtt ggt gtt caa gga ccc cct ggc cct gct gga<br>Gly Glu Pro Gly Pro Val Gly Val Gln Gly Pro Pro Gly Pro Ala Gly<br>450                  455                     460 | 1511 | |
| gag gaa gga aag cga gga gct cga ggt gaa ccc gga ccc act ggc ctg<br>Glu Glu Gly Lys Arg Gly Ala Arg Gly Glu Pro Gly Pro Thr Gly Leu<br>465                  470                     475                   480 | 1559 | |
| ccc gga ccc cct ggc gag cgt ggt gga cct ggt agc cgt ggt ttc cct | 1607 | |

-continued

| | | | | | | | | | | | | |
|---|---|---|---|---|---|---|---|---|---|---|---|---|
|Pro|Gly|Pro|Pro|Gly|Glu|Arg|Gly|Gly|Pro|Gly|Ser|Arg|Gly|Phe|Pro|
| | | |485| | | |490| | | |495| |

```
ggc gca gat ggt gtt gct ggt ccc aag ggt ccc gct ggt gaa cgt ggt    1655
Gly Ala Asp Gly Val Ala Gly Pro Lys Gly Pro Ala Gly Glu Arg Gly
        500                 505                 510 tct cct ggc ccc gct ggc ccc aaa gga tct cct ggt gaa gct ggt cgt    1703
Ser Pro Gly Pro Ala Gly Pro Lys Gly Ser Pro Gly Glu Ala Gly Arg
            515                 520                 525 ccc ggt gaa gct ggt ctg cct ggt gcc aag ggt ctg act gga agc cct    1751
Pro Gly Glu Ala Gly Leu Pro Gly Ala Lys Gly Leu Thr Gly Ser Pro
530                 535                 540 ggc agc cct ggt cct gat ggc aaa act ggc ccc cct ggt ccc gcc ggt    1799
Gly Ser Pro Gly Pro Asp Gly Lys Thr Gly Pro Pro Gly Pro Ala Gly
545                 550                 555                 560 caa gat ggt cgc ccc gga ccc cca ggc cca cct ggt gcc cgt ggt cag    1847
Gln Asp Gly Arg Pro Gly Pro Pro Gly Pro Pro Gly Ala Arg Gly Gln
                565                 570                 575 gct ggt gtg atg gga ttc cct gga cct aaa ggt gct gct gga gag ccc    1895
Ala Gly Val Met Gly Phe Pro Gly Pro Lys Gly Ala Ala Gly Glu Pro
            580                 585                 590 ggc aag gct gga gag cga ggt gtt ccc gga ccc cct ggc gct gtc ggt    1943
Gly Lys Ala Gly Glu Arg Gly Val Pro Gly Pro Pro Gly Ala Val Gly
        595                 600                 605 cct gct ggc aaa gat gga gag gct gga gct cag gga ccc cct ggc cct    1991
Pro Ala Gly Lys Asp Gly Glu Ala Gly Ala Gln Gly Pro Pro Gly Pro
610                 615                 620 gct ggt ccc gct ggc gag aga ggt gaa caa ggc cct gct ggc tcc ccc    2039
Ala Gly Pro Ala Gly Glu Arg Gly Glu Gln Gly Pro Ala Gly Ser Pro
625                 630                 635                 640 gga ttc cag ggt ctc cct ggt cct gct ggt cct cca ggt gaa gca ggc    2087
Gly Phe Gln Gly Leu Pro Gly Pro Ala Gly Pro Pro Gly Glu Ala Gly
                645                 650                 655 aaa cct ggt gaa cag ggt gtt cct gga gac ctt ggc gcc cct ggc ccc    2135
Lys Pro Gly Glu Gln Gly Val Pro Gly Asp Leu Gly Ala Pro Gly Pro
            660                 665                 670 tct gga gca aga ggc gag aga ggt ttc cct ggc gag cgt ggt gtg caa    2183
Ser Gly Ala Arg Gly Glu Arg Gly Phe Pro Gly Glu Arg Gly Val Gln
        675                 680                 685 ggt ccc cct ggt cct gct gga ccc cga ggg gcc aac ggt gct ccc ggc    2231
Gly Pro Pro Gly Pro Ala Gly Pro Arg Gly Ala Asn Gly Ala Pro Gly
690                 695                 700 aac gat ggt gct aag ggt gat gct ggt gcc cct gga gct ccc ggt agc    2279
Asn Asp Gly Ala Lys Gly Asp Ala Gly Ala Pro Gly Ala Pro Gly Ser
705                 710                 715                 720 cag ggc gcc cct ggc ctt cag gga atg cct ggt gaa cgt ggt gca gct    2327
Gln Gly Ala Pro Gly Leu Gln Gly Met Pro Gly Glu Arg Gly Ala Ala
                725                 730                 735 ggt ctt cca ggg cct aag ggt gac aga ggt gat gct ggt ccc aaa ggt    2375
Gly Leu Pro Gly Pro Lys Gly Asp Arg Gly Asp Ala Gly Pro Lys Gly
            740                 745                 750 gct gat ggc tct cct ggc aaa gat ggc gtc cgt ggt ctg acc ggc ccc    2423
Ala Asp Gly Ser Pro Gly Lys Asp Gly Val Arg Gly Leu Thr Gly Pro
        755                 760                 765 att ggt cct cct ggc cct gct ggt gcc cct ggt gac aag ggt gaa agt    2471
Ile Gly Pro Pro Gly Pro Ala Gly Ala Pro Gly Asp Lys Gly Glu Ser
770                 775                 780 ggt ccc agc ggc cct gct ggt ccc act gga gct cgt ggt gcc ccc gga    2519
Gly Pro Ser Gly Pro Ala Gly Pro Thr Gly Ala Arg Gly Ala Pro Gly
785                 790                 795                 800 gac cgt ggt gag cct ggt ccc ccc ggc cct gct ggc ttt gct ggc ccc    2567
```

```
                Asp Arg Gly Glu Pro Gly Pro Pro Gly Pro Ala Gly Phe Ala Gly Pro
                                805                 810                 815 cct ggt gct gac ggc caa cct ggt gct aaa ggc gaa cct ggt gat gct        2615
Pro Gly Ala Asp Gly Gln Pro Gly Ala Lys Gly Glu Pro Gly Asp Ala
            820                 825                 830 ggt gcc aaa ggc gat gct ggt ccc cct ggg cct gcc gga ccc gct gga        2663
Gly Ala Lys Gly Asp Ala Gly Pro Pro Gly Pro Ala Gly Pro Ala Gly
        835                 840                 845 ccc cct ggc ccc att ggt aat gtt ggt gct cct gga gcc aaa ggt gct        2711
Pro Pro Gly Pro Ile Gly Asn Val Gly Ala Pro Gly Ala Lys Gly Ala
    850                 855                 860 cgc ggc agc gct ggt ccc cct ggt gct act ggt ttc cct ggt gct gct        2759
Arg Gly Ser Ala Gly Pro Pro Gly Ala Thr Gly Phe Pro Gly Ala Ala
865                 870                 875                 880 ggc cga gtc ggt cct cct ggc ccc tct gga aat gct gga ccc cct ggc        2807
Gly Arg Val Gly Pro Pro Gly Pro Ser Gly Asn Ala Gly Pro Pro Gly
                885                 890                 895 cct cct ggt cct gct ggc aaa gaa ggc ggc aaa ggt ccc cgt ggt gag        2855
Pro Pro Gly Pro Ala Gly Lys Glu Gly Gly Lys Gly Pro Arg Gly Glu
            900                 905                 910 act ggc cct gct gga cgt cct ggt gaa gtt ggt ccc cct ggt ccc cct        2903
Thr Gly Pro Ala Gly Arg Pro Gly Glu Val Gly Pro Pro Gly Pro Pro
        915                 920                 925 ggc cct gct ggc gag aaa gga tcc cct ggt gct gat ggt cct gct ggt        2951
Gly Pro Ala Gly Glu Lys Gly Ser Pro Gly Ala Asp Gly Pro Ala Gly
    930                 935                 940 gct cct ggt act ccc ggg cct caa ggt att gct gga cag cgt ggt gtg        2999
Ala Pro Gly Thr Pro Gly Pro Gln Gly Ile Ala Gly Gln Arg Gly Val
945                 950                 955                 960 gtc ggc ctg cct ggt cag aga gga gag aga ggc ttc cct ggt ctt cct        3047
Val Gly Leu Pro Gly Gln Arg Gly Glu Arg Gly Phe Pro Gly Leu Pro
                965                 970                 975 ggc ccc tct ggt gaa cct ggc aaa caa ggt ccc tct gga gca agt ggt        3095
Gly Pro Ser Gly Glu Pro Gly Lys Gln Gly Pro Ser Gly Ala Ser Gly
            980                 985                 990 gaa cgt ggt ccc ccc ggt ccc atg ggc ccc cct gga ttg gct gga ccc        3143
Glu Arg Gly Pro Pro Gly Pro Met Gly Pro Pro Gly Leu Ala Gly Pro
        995                 1000                1005 cct ggt gaa tct gga cgt gag ggg gct cct gct gcc gaa ggt tcc cct        3191
Pro Gly Glu Ser Gly Arg Glu Gly Ala Pro Ala Ala Glu Gly Ser Pro
    1010                1015                1020 gga cga gac ggt tct cct ggc gcc aag ggt gac cgt ggt gag acc ggc        3239
Gly Arg Asp Gly Ser Pro Gly Ala Lys Gly Asp Arg Gly Glu Thr Gly
1025                1030                1035                1040 ccc gct gga ccc cct ggt gct cct ggt gct cct ggt gcc cct ggc ccc        3287
Pro Ala Gly Pro Pro Gly Ala Pro Gly Ala Pro Gly Ala Pro Gly Pro
                1045                1050                1055 gtt ggc cct gct ggc aag agt ggt gat cgt ggt gag act ggt cct gct        3335
Val Gly Pro Ala Gly Lys Ser Gly Asp Arg Gly Glu Thr Gly Pro Ala
            1060                1065                1070 ggt ccc gcc ggt ccc gtc ggc ccc gtc ggc gcc cgt ggc ccc gcc gga        3383
Gly Pro Ala Gly Pro Val Gly Pro Val Gly Ala Arg Gly Pro Ala Gly
        1075                1080                1085 ccc caa ggc ccc cgt ggt gac aag ggt gag aca ggc gaa cag ggc gac        3431
Pro Gln Gly Pro Arg Gly Asp Lys Gly Glu Thr Gly Glu Gln Gly Asp
    1090                1095                1100 aga ggc ata aag ggt cac cgt ggc ttc tct ggc ctc cag ggt ccc cct        3479
Arg Gly Ile Lys Gly His Arg Gly Phe Ser Gly Leu Gln Gly Pro Pro
1105                1110                1115                1120 ggc cct cct ggc tct cct ggt gaa caa ggt ccc tct gga gcc tct ggt        3527
```

-continued

|     |     |
| --- | --- |
| Gly Pro Pro Gly Ser Pro Gly Glu Gln Gly Pro Ser Gly Ala Ser Gly<br>           1125                1130                1135 | |
| cct gct ggt ccc cga ggt ccc cct ggc tct gct ggt gct cct ggc aaa<br>Pro Ala Gly Pro Arg Gly Pro Pro Gly Ser Ala Gly Ala Pro Gly Lys<br>           1140               1145                1150 | 3575 |
| gat gga ctc aac ggt ctc cct ggc ccc att ggg ccc cct ggt cct cgc<br>Asp Gly Leu Asn Gly Leu Pro Gly Pro Ile Gly Pro Pro Gly Pro Arg<br>           1155               1160                1165 | 3623 |
| ggt cgc act ggt gat gct ggt cct gtt ggt ccc ccc ggc cct cct gga<br>Gly Arg Thr Gly Asp Ala Gly Pro Val Gly Pro Pro Gly Pro Pro Gly<br>           1170               1175                1180 | 3671 |
| cct cct ggt ccc cct ggt cct ccc agc gct ggt ttc gac ttc agc ttc<br>Pro Pro Gly Pro Pro Gly Pro Pro Ser Ala Gly Phe Asp Phe Ser Phe<br>1185                1190               1195                1200 | 3719 |
| ctg ccc cag cca cct caa gag aag gct cac gat ggt ggc cgc tac tac<br>Leu Pro Gln Pro Pro Gln Glu Lys Ala His Asp Gly Gly Arg Tyr Tyr<br>           1205               1210                1215 | 3767 |
| cgg gct gat gat gcc aat gtg gtt cgt gac cgt gac ctc gag gtg gac<br>Arg Ala Asp Asp Ala Asn Val Val Arg Asp Arg Asp Leu Glu Val Asp<br>         1220               1225                1230 | 3815 |
| acc acc ctc aag agc ctg agc cag cag atc gag aac atc cgg agc cca<br>Thr Thr Leu Lys Ser Leu Ser Gln Gln Ile Glu Asn Ile Arg Ser Pro<br>           1235               1240                1245 | 3863 |
| gag gga agc cgc aag aac ccc gcc cgc acc tgc cgt gac ctc aag atg<br>Glu Gly Ser Arg Lys Asn Pro Ala Arg Thr Cys Arg Asp Leu Lys Met<br>   1250               1255                1260 | 3911 |
| tgc cac tct gac tgg aag agt gga gag tac tgg att gac ccc aac caa<br>Cys His Ser Asp Trp Lys Ser Gly Glu Tyr Trp Ile Asp Pro Asn Gln<br>1265                1270               1275                1280 | 3959 |
| ggc tgc aac ctg gat gcc atc aaa gtc ttc tgc aac atg gag act ggt<br>Gly Cys Asn Leu Asp Ala Ile Lys Val Phe Cys Asn Met Glu Thr Gly<br>           1285               1290                1295 | 4007 |
| gag acc tgc gtg tac ccc act cag ccc agt gtg gcc cag aag aac tgg<br>Glu Thr Cys Val Tyr Pro Thr Gln Pro Ser Val Ala Gln Lys Asn Trp<br>         1300               1305                1310 | 4055 |
| tac atc agc aag aac ccc aag gac aag agg cat gtc tgg ttc ggc gag<br>Tyr Ile Ser Lys Asn Pro Lys Asp Lys Arg His Val Trp Phe Gly Glu<br>           1315               1320                1325 | 4103 |
| agc atg acc gat gga ttc cag ttc gag tat ggc ggc cag ggc tcc gac<br>Ser Met Thr Asp Gly Phe Gln Phe Glu Tyr Gly Gly Gln Gly Ser Asp<br>         1330               1335                1340 | 4151 |
| cct gcc gat gtg gcc atc cag ctg acc ttc ctg cgc ctg atg tcc acc<br>Pro Ala Asp Val Ala Ile Gln Leu Thr Phe Leu Arg Leu Met Ser Thr<br>1345                1350               1355                1360 | 4199 |
| gag gcc tcc cag aac atc acc tac cac tgc aag aac agc gtg gcc tac<br>Glu Ala Ser Gln Asn Ile Thr Tyr His Cys Lys Asn Ser Val Ala Tyr<br>           1365               1370                1375 | 4247 |
| atg gac cag cag act ggc aac ctc aag aag gcc ctg ctc ctc aag ggc<br>Met Asp Gln Gln Thr Gly Asn Leu Lys Lys Ala Leu Leu Leu Lys Gly<br>         1380               1385                1390 | 4295 |
| tcc aac gag atc gag atc cgc gcc gag ggc aac agc cgc ttc acc tac<br>Ser Asn Glu Ile Glu Ile Arg Ala Glu Gly Asn Ser Arg Phe Thr Tyr<br>           1395               1400                1405 | 4343 |
| agc gtc act gtc gat ggc tgc acg agt cac acc gga gcc tgg ggc aag<br>Ser Val Thr Val Asp Gly Cys Thr Ser His Thr Gly Ala Trp Gly Lys<br>          1410               1415                1420 | 4391 |
| aca gtg att gaa tac aaa acc acc aag tcc tcc cgc ctg ccc atc atc<br>Thr Val Ile Glu Tyr Lys Thr Thr Lys Ser Ser Arg Leu Pro Ile Ile<br>1425                1430               1435                1440 | 4439 |
| gat gtg gcc ccc ttg gac gtt ggt gcc cca gac cag gaa ttc ggc ttc | 4487 |

```
Asp Val Ala Pro Leu Asp Val Gly Ala Pro Asp Gln Glu Phe Gly Phe
                1445                1450                1455
gac gtt ggc cct gtc tgc ttc ctg taaactccct ccatcccaac ctggctccct       4541
Asp Val Gly Pro Val Cys Phe Leu
                1460 cccacccaac caactttccc cccaacccgg aaacagacaa gcaacccaaa ctgaaccccc      4601 ccaaaagcca aaaatgggga gacaatttca catggacttt ggaaatatt tttttccttt       4661 gcattcatct ctcaaactta gttttatct ttgaccaacc gaacatgacc aaaaaccaaa       4721 agtgcattca accttaccaa aaaaaaaaa aaaaaaaaa gaataaataa ataagttttt        4781 aaaaaaggaa gcttggtcca cttgcttgaa gacccatgcg ggggtaagtc cctttctgcc      4841 cgttgggtta tgaaacccca atgctgccct ttctgctcct ttctccacac ccccttggc      4901 ctccccctcca ctccttccca aatctgtctc cccagaagac acaggaaaca atgtattgtc    4961 tgcccagcaa tcaaaggcaa tgctcaaaca cccaagtggc ccccaccctc agcccgctcc     5021 tgcccgccca gcaccccccag gccctgggga cctggggttc tcagactgcc aaagaagcct   5081 tgccatctgg cgctcccatg gctcttgcaa catctcccct tcgttttga gggggtcatg      5141 ccggggggagc caccagcccc tcactgggtt cggaggagag tcaggaaggg ccacgacaaa    5201 gcagaaacat cggatttggg gaacgcgtgt catcccttgt gccgcaggct gggcgggaga    5261 gactgttctg ttctgttcct tgtgtaactg tgttgctgaa agactacctc gttcttgtct    5321 tgatgtgtca ccggggcaac tgcctggggg cggggatggg ggcagggtgg aagcggctcc    5381 ccatttttat accaaaggtg ctacatctat gtgatgggtg gggtggggag ggaatcactg    5441 gtgctataga aattgagatg cccccccagg ccagcaaatg ttccttttg ttcaaagtct     5501 attttattc cttgatattt tttctttctt tttttttt ttttgtggatg gggacttgtg      5561 aatttttcta aaggtgctat ttaacatggg aggagagcgt gtgcgctcca gcccagcccg    5621 ctgctcactt tccaccctct ctccacctgc ctctggcttc tcaggcctct gctctccgac    5681 ctctctcctc tgaaaccctc ctccacagct gcagcccatc ctcccggctc cctcctagtc    5741 tgtcctgcgt cctctgtccc cgggtttcag agacaacttc ccaaagcaca aagcagtttt    5801 tccctagggg tgggaggaag caaaagactc tgtaccatt ttgtatgtgt ataataattt     5861 gagatgtttt taattatttt gattgctgga ataaagcatg tggaaatgac ccaaacataa    5921 tccgcagtgg cctcctaatt tccttcttg gagttggggg aggggtagac atggggaagg    5981 ggccttgggg tgatgggctt gcttccatt cctgcccttt cctcccccac tattctcttc     6041 tagatccctc cataacccca ctcccctttc tctcaccctt cttataccgc aaacctttct    6101 acttcctctt tcattttcta ttcttgcaat ttccttgcac cttttccaaa tcctcttctc    6161 ccctgcaata ccatacaggc aatccacgtg cacaacacac acacacactc ttcacatctg    6221 gggttgtcca aacctcatac ccactcccct tcaagcccat ccactctcca cccctggat    6281 gccctgcact tggtggcggt gggatgctca tggatactgg gagggtgagg ggagtggaac    6341 ccgtgaggag gacctggggg cctctccttg aactgacatg aagggtcatc tggcctctgc    6401 tcccttctca cccacgctga cctcctgccg aaggagcaac gcaacaggag aggggtctgc    6461 tgagcctggc gagggtctgg gagggaccag gaggaaggcg tgctccctgc tcgctgtcct    6521 ggccctgggg gagtgaggga gacagacacc tgggagagct gtgggggaagg cactcgcacc   6581 gtgctcttgg gaaggaagga gacctggccc tgctcaccac ggactgggtg cctcgacctc    6641 ctgaatcccc agaacacaac ccccctgggc tggggtggtc tggggaacca tcgtgccccc    6701 gcctcccgcc tactccttt taagctt                                         6728
```

```
<210> SEQ ID NO 2
<211> LENGTH: 1464
<212> TYPE: PRT
<213> ORGANISM: Homo sapiens

<400> SEQUENCE: 2
```

| | | | | | | | | | | | | | | | |
|---|---|---|---|---|---|---|---|---|---|---|---|---|---|---|---|
| Met | Phe | Ser | Phe | Val | Asp | Leu | Arg | Leu | Leu | Leu | Leu | Leu | Ala | Ala | Thr |
| 1 | | | | 5 | | | | | 10 | | | | | 15 | |
| Ala | Leu | Leu | Thr | His | Gly | Gln | Glu | Glu | Gly | Gln | Val | Glu | Gly | Gln | Asp |
| | | | 20 | | | | | 25 | | | | | 30 | | |
| Glu | Asp | Ile | Pro | Pro | Ile | Thr | Cys | Val | Gln | Asn | Gly | Leu | Arg | Tyr | His |
| | | 35 | | | | | 40 | | | | | 45 | | | |
| Asp | Arg | Asp | Val | Trp | Lys | Pro | Glu | Pro | Cys | Arg | Ile | Cys | Val | Cys | Asp |
| | 50 | | | | | 55 | | | | | 60 | | | | |
| Asn | Gly | Lys | Val | Leu | Cys | Asp | Asp | Val | Ile | Cys | Asp | Glu | Thr | Lys | Asn |
| 65 | | | | | 70 | | | | | 75 | | | | | 80 |
| Cys | Pro | Gly | Ala | Glu | Val | Pro | Glu | Gly | Glu | Cys | Cys | Pro | Val | Cys | Pro |
| | | | | 85 | | | | | 90 | | | | | 95 | |
| Asp | Gly | Ser | Glu | Ser | Pro | Thr | Asp | Gln | Glu | Thr | Thr | Gly | Val | Glu | Gly |
| | | | 100 | | | | | 105 | | | | | 110 | | |
| Pro | Lys | Gly | Asp | Thr | Gly | Pro | Arg | Gly | Pro | Arg | Gly | Pro | Ala | Gly | Pro |
| | | 115 | | | | | 120 | | | | | 125 | | | |
| Pro | Gly | Arg | Asp | Gly | Ile | Pro | Gly | Gln | Pro | Gly | Leu | Pro | Gly | Pro | Pro |
| | 130 | | | | | 135 | | | | | 140 | | | | |
| Gly | Pro | Pro | Gly | Pro | Pro | Gly | Pro | Pro | Gly | Leu | Gly | Gly | Asn | Phe | Ala |
| 145 | | | | | 150 | | | | | 155 | | | | | 160 |
| Pro | Gln | Leu | Ser | Tyr | Gly | Tyr | Asp | Glu | Lys | Ser | Thr | Gly | Gly | Ile | Ser |
| | | | | 165 | | | | | 170 | | | | | 175 | |
| Val | Pro | Gly | Pro | Met | Gly | Pro | Ser | Gly | Pro | Arg | Gly | Leu | Pro | Gly | Pro |
| | | | 180 | | | | | 185 | | | | | 190 | | |
| Pro | Gly | Ala | Pro | Gly | Pro | Gln | Gly | Phe | Gln | Gly | Pro | Pro | Gly | Glu | Pro |
| | | 195 | | | | | 200 | | | | | 205 | | | |
| Gly | Glu | Pro | Gly | Ala | Ser | Gly | Pro | Met | Gly | Pro | Arg | Gly | Pro | Pro | Gly |
| | 210 | | | | | 215 | | | | | 220 | | | | |
| Pro | Pro | Gly | Lys | Asn | Gly | Asp | Asp | Gly | Glu | Ala | Gly | Lys | Pro | Gly | Arg |
| 225 | | | | | 230 | | | | | 235 | | | | | 240 |
| Pro | Gly | Glu | Arg | Gly | Pro | Pro | Gly | Pro | Gln | Gly | Ala | Arg | Gly | Leu | Pro |
| | | | | 245 | | | | | 250 | | | | | 255 | |
| Gly | Thr | Ala | Gly | Leu | Pro | Gly | Met | Lys | Gly | His | Arg | Gly | Phe | Ser | Gly |
| | | | 260 | | | | | 265 | | | | | 270 | | |
| Leu | Asp | Gly | Ala | Lys | Gly | Asp | Ala | Gly | Pro | Ala | Gly | Pro | Lys | Gly | Glu |
| | | 275 | | | | | 280 | | | | | 285 | | | |
| Pro | Gly | Ser | Pro | Gly | Glu | Asn | Gly | Ala | Pro | Gly | Gln | Met | Gly | Pro | Arg |
| | 290 | | | | | 295 | | | | | 300 | | | | |
| Gly | Leu | Pro | Gly | Glu | Arg | Gly | Arg | Pro | Gly | Ala | Pro | Gly | Pro | Ala | Gly |
| 305 | | | | | 310 | | | | | 315 | | | | | 320 |
| Ala | Arg | Gly | Asn | Asp | Gly | Ala | Thr | Gly | Ala | Ala | Gly | Pro | Pro | Gly | Pro |
| | | | | 325 | | | | | 330 | | | | | 335 | |
| Thr | Gly | Pro | Ala | Gly | Pro | Pro | Gly | Phe | Pro | Gly | Ala | Val | Gly | Ala | Lys |
| | | | 340 | | | | | 345 | | | | | 350 | | |
| Gly | Glu | Ala | Gly | Pro | Gln | Gly | Pro | Arg | Gly | Ser | Glu | Gly | Pro | Gln | Gly |
| | | 355 | | | | | 360 | | | | | 365 | | | |
| Val | Arg | Gly | Glu | Pro | Gly | Pro | Pro | Gly | Pro | Ala | Gly | Ala | Ala | Gly | Pro |
| | 370 | | | | | 375 | | | | | 380 | | | | |

```
Ala Gly Asn Pro Gly Ala Asp Gly Gln Pro Gly Ala Lys Ala Asn
385                 390                 395                 400

Gly Ala Pro Gly Ile Ala Gly Ala Pro Gly Phe Pro Gly Ala Arg Gly
            405                 410                 415

Pro Ser Gly Pro Gln Gly Pro Gly Pro Pro Gly Pro Lys Gly Asn
            420                 425                 430

Ser Gly Glu Pro Gly Ala Pro Gly Ser Lys Gly Asp Thr Gly Ala Lys
            435                 440                 445

Gly Glu Pro Gly Pro Val Gly Val Gln Gly Pro Pro Gly Pro Ala Gly
            450                 455                 460

Glu Glu Gly Lys Arg Gly Ala Arg Gly Glu Pro Gly Pro Thr Gly Leu
465                 470                 475                 480

Pro Gly Pro Pro Gly Glu Arg Gly Gly Pro Gly Ser Arg Gly Phe Pro
            485                 490                 495

Gly Ala Asp Gly Val Ala Gly Pro Lys Gly Pro Ala Gly Glu Arg Gly
            500                 505                 510

Ser Pro Gly Pro Ala Gly Pro Lys Gly Ser Pro Gly Glu Ala Gly Arg
            515                 520                 525

Pro Gly Glu Ala Gly Leu Pro Gly Ala Lys Gly Leu Thr Gly Ser Pro
            530                 535                 540

Gly Ser Pro Gly Pro Asp Gly Lys Thr Gly Pro Pro Gly Pro Ala Gly
545                 550                 555                 560

Gln Asp Gly Arg Pro Gly Pro Pro Gly Pro Pro Gly Ala Arg Gly Gln
            565                 570                 575

Ala Gly Val Met Gly Phe Pro Gly Pro Lys Gly Ala Ala Gly Glu Pro
            580                 585                 590

Gly Lys Ala Gly Glu Arg Gly Val Pro Gly Pro Pro Gly Ala Val Gly
            595                 600                 605

Pro Ala Gly Lys Asp Gly Glu Ala Gly Ala Gln Gly Pro Pro Gly Pro
            610                 615                 620

Ala Gly Pro Ala Gly Glu Arg Gly Glu Gln Gly Pro Ala Gly Ser Pro
625                 630                 635                 640

Gly Phe Gln Gly Leu Pro Gly Pro Ala Gly Pro Pro Gly Glu Ala Gly
            645                 650                 655

Lys Pro Gly Glu Gln Gly Val Pro Gly Asp Leu Gly Ala Pro Gly Pro
            660                 665                 670

Ser Gly Ala Arg Gly Glu Arg Gly Phe Pro Gly Glu Arg Gly Val Gln
            675                 680                 685

Gly Pro Pro Gly Pro Ala Gly Pro Arg Gly Ala Asn Gly Ala Pro Gly
            690                 695                 700

Asn Asp Gly Ala Lys Gly Asp Ala Gly Ala Pro Gly Ala Pro Gly Ser
705                 710                 715                 720

Gln Gly Ala Pro Gly Leu Gln Gly Met Pro Gly Glu Arg Gly Ala Ala
            725                 730                 735

Gly Leu Pro Gly Pro Lys Gly Asp Arg Gly Asp Ala Gly Pro Lys Gly
            740                 745                 750

Ala Asp Gly Ser Pro Gly Lys Asp Gly Val Arg Gly Leu Thr Gly Pro
            755                 760                 765

Ile Gly Pro Pro Gly Pro Ala Gly Ala Pro Gly Asp Lys Gly Glu Ser
            770                 775                 780

Gly Pro Ser Gly Pro Ala Gly Pro Thr Gly Ala Arg Gly Ala Pro Gly
785                 790                 795                 800

Asp Arg Gly Glu Pro Gly Pro Pro Gly Pro Ala Gly Phe Ala Gly Pro
```

-continued

```
            805                 810                 815
Pro Gly Ala Asp Gly Gln Pro Gly Ala Lys Gly Glu Pro Gly Asp Ala
            820                 825                 830

Gly Ala Lys Gly Asp Ala Gly Pro Gly Pro Ala Gly Pro Ala Gly
            835                 840                 845

Pro Pro Gly Pro Ile Gly Asn Val Gly Ala Pro Gly Ala Lys Gly Ala
            850                 855                 860

Arg Gly Ser Ala Gly Pro Pro Gly Ala Thr Gly Phe Pro Gly Ala Ala
865                 870                 875                 880

Gly Arg Val Gly Pro Pro Gly Ser Gly Asn Ala Gly Pro Pro Gly
            885                 890                 895

Pro Pro Gly Pro Ala Gly Lys Glu Gly Gly Lys Gly Pro Arg Gly Glu
            900                 905                 910

Thr Gly Pro Ala Gly Arg Pro Gly Glu Val Gly Pro Pro Gly Pro Pro
            915                 920                 925

Gly Pro Ala Gly Glu Lys Gly Ser Pro Gly Ala Asp Gly Pro Ala Gly
            930                 935                 940

Ala Pro Gly Thr Pro Gly Pro Gln Gly Ile Ala Gly Gln Arg Gly Val
945                 950                 955                 960

Val Gly Leu Pro Gly Gln Arg Gly Glu Arg Gly Phe Pro Gly Leu Pro
            965                 970                 975

Gly Pro Ser Gly Glu Pro Gly Lys Gln Gly Pro Ser Gly Ala Ser Gly
            980                 985                 990

Glu Arg Gly Pro Pro Gly Pro Met Gly Pro Pro Gly Leu Ala Gly Pro
            995                 1000                1005

Pro Gly Glu Ser Gly Arg Glu Gly Ala Pro Ala Glu Gly Ser Pro
    1010                1015                1020

Gly Arg Asp Gly Ser Pro Gly Ala Lys Gly Asp Arg Gly Glu Thr Gly
1025                1030                1035                1040

Pro Ala Gly Pro Pro Gly Ala Pro Gly Ala Pro Gly Ala Pro Gly Pro
            1045                1050                1055

Val Gly Pro Ala Gly Lys Ser Gly Asp Arg Gly Glu Thr Gly Pro Ala
            1060                1065                1070

Gly Pro Ala Gly Pro Val Gly Pro Val Gly Ala Arg Gly Pro Ala Gly
            1075                1080                1085

Pro Gln Gly Pro Arg Gly Asp Lys Gly Glu Thr Gly Glu Gln Gly Asp
    1090                1095                1100

Arg Gly Ile Lys Gly His Arg Gly Phe Ser Gly Leu Gln Gly Pro Pro
1105                1110                1115                1120

Gly Pro Pro Gly Ser Pro Gly Glu Gln Gly Pro Ser Gly Ala Ser Gly
            1125                1130                1135

Pro Ala Gly Pro Arg Gly Pro Pro Gly Ser Ala Gly Ala Pro Gly Lys
            1140                1145                1150

Asp Gly Leu Asn Gly Leu Pro Gly Pro Ile Gly Pro Pro Gly Pro Arg
    1155                1160                1165

Gly Arg Thr Gly Asp Ala Gly Pro Val Gly Pro Pro Gly Pro Pro Gly
    1170                1175                1180

Pro Pro Gly Pro Pro Gly Pro Pro Ser Ala Gly Phe Asp Phe Ser Phe
1185                1190                1195                1200

Leu Pro Gln Pro Pro Gln Glu Lys Ala His Asp Gly Gly Arg Tyr Tyr
    1205                1210                1215

Arg Ala Asp Asp Ala Asn Val Val Arg Asp Arg Asp Leu Glu Val Asp
        1220                1225                1230
```

```
Thr Thr Leu Lys Ser Leu Ser Gln Gln Ile Glu Asn Ile Arg Ser Pro
        1235                1240                1245

Glu Gly Ser Arg Lys Asn Pro Ala Arg Thr Cys Arg Asp Leu Lys Met
    1250                1255                1260

Cys His Ser Asp Trp Lys Ser Gly Glu Tyr Trp Ile Asp Pro Asn Gln
1265                1270                1275                1280

Gly Cys Asn Leu Asp Ala Ile Lys Val Phe Cys Asn Met Glu Thr Gly
            1285                1290                1295

Glu Thr Cys Val Tyr Pro Thr Gln Pro Ser Val Ala Gln Lys Asn Trp
    1300                1305                1310

Tyr Ile Ser Lys Asn Pro Lys Asp Lys Arg His Val Trp Phe Gly Glu
        1315                1320                1325

Ser Met Thr Asp Gly Phe Gln Phe Glu Tyr Gly Gly Gln Gly Ser Asp
    1330                1335                1340

Pro Ala Asp Val Ala Ile Gln Leu Thr Phe Leu Arg Leu Met Ser Thr
1345                1350                1355                1360

Glu Ala Ser Gln Asn Ile Thr Tyr His Cys Lys Asn Ser Val Ala Tyr
            1365                1370                1375

Met Asp Gln Gln Thr Gly Asn Leu Lys Lys Ala Leu Leu Leu Lys Gly
        1380                1385                1390

Ser Asn Glu Ile Glu Ile Arg Ala Glu Gly Asn Ser Arg Phe Thr Tyr
    1395                1400                1405

Ser Val Thr Val Asp Gly Cys Thr Ser His Thr Gly Ala Trp Gly Lys
    1410                1415                1420

Thr Val Ile Glu Tyr Lys Thr Thr Lys Ser Ser Arg Leu Pro Ile Ile
1425                1430                1435                1440

Asp Val Ala Pro Leu Asp Val Gly Ala Pro Asp Gln Glu Phe Gly Phe
            1445                1450                1455

Asp Val Gly Pro Val Cys Phe Leu
        1460

<210> SEQ ID NO 3
<211> LENGTH: 20
<212> TYPE: DNA
<213> ORGANISM: Homo sapiens
<220> FEATURE:
<223> OTHER INFORMATION: Antisense oligonucleotide

<400> SEQUENCE: 3
ggacgaccag gttttccagc                                              20

<210> SEQ ID NO 4
<211> LENGTH: 20
<212> TYPE: DNA
<213> ORGANISM: Homo sapiens
<220> FEATURE:
<223> OTHER INFORMATION: Antisense oligonucleotide

<400> SEQUENCE: 4
gcagcaccag cagggccagg                                              20

<210> SEQ ID NO 5
<211> LENGTH: 20
<212> TYPE: DNA
<213> ORGANISM: Homo sapiens
<220> FEATURE:
<223> OTHER INFORMATION: Antisense oligonucleotide

<400> SEQUENCE: 5
gccaggagca ccaggttcac                                              20
```

```
<210> SEQ ID NO 6
<211> LENGTH: 20
<212> TYPE: DNA
<213> ORGANISM: Homo sapiens
<220> FEATURE:
<223> OTHER INFORMATION: Antisense oligonucleotide

<400> SEQUENCE: 6
cttcctctcc agcagggcca                                                   20

<210> SEQ ID NO 7
<211> LENGTH: 20
<212> TYPE: DNA
<213> ORGANISM: Homo sapiens
<220> FEATURE:
<223> OTHER INFORMATION: Antisense oligonucleotide

<400> SEQUENCE: 7
gccttgccgg gctctccagc                                                   20

<210> SEQ ID NO 8
<211> LENGTH: 20
<212> TYPE: DNA
<213> ORGANISM: Homo sapiens
<220> FEATURE:
<223> OTHER INFORMATION: Antisense oligonucleotide

<400> SEQUENCE: 8
cgggaacacc tcgctctcca                                                   20

<210> SEQ ID NO 9
<211> LENGTH: 20
<212> TYPE: DNA
<213> ORGANISM: Homo sapiens
<220> FEATURE:
<223> OTHER INFORMATION: Antisense oligonucleotide

<400> SEQUENCE: 9
gcaggaccga cagcgccagg                                                   20

<210> SEQ ID NO 10
<211> LENGTH: 20
<212> TYPE: DNA
<213> ORGANISM: Homo sapiens
<220> FEATURE:
<223> OTHER INFORMATION: Antisense oligonucleotide

<400> SEQUENCE: 10
tccatctttg ccagcaggac                                                   20

<210> SEQ ID NO 11
<211> LENGTH: 20
<212> TYPE: DNA
<213> ORGANISM: Homo sapiens
<220> FEATURE:
<223> OTHER INFORMATION: Antisense oligonucleotide

<400> SEQUENCE: 11
ggtccctgag ctccagcctc                                                   20

<210> SEQ ID NO 12
<211> LENGTH: 19
<212> TYPE: DNA
<213> ORGANISM: Homo sapiens
<220> FEATURE:
<223> OTHER INFORMATION: Antisense oligonucleotide
```

```
<400> SEQUENCE: 12
ttggccgtca gcaccaggg                                                  19

<210> SEQ ID NO 13
<211> LENGTH: 20
<212> TYPE: DNA
<213> ORGANISM: Homo sapiens
<220> FEATURE:
<223> OTHER INFORMATION: Antisense oligonucleotide

<400> SEQUENCE: 13
tttctcgcca gcagggccag                                                 20

<210> SEQ ID NO 14
<211> LENGTH: 20
<212> TYPE: DNA
<213> ORGANISM: Homo sapiens
<220> FEATURE:
<223> OTHER INFORMATION: Antisense oligonucleotide

<400> SEQUENCE: 14
ctcgatctgc tggctcaggc                                                 20
```

CHEMOTHERAPY INVOLVING ANTISENSE OLIGONUCLEOTIDES FOR PREVENTING AND/OR TREATING PULMONARY FIBROSIS

RELATED APPLICATIONS

This application is a continuation-in-part of U.S. patent application Ser. No. 11/021,603, filed Dec. 21, 2004 now U.S. Pat. No. 7,396,823, for Rahul K. Nath, et al, which is a continuation-in-part of U.S. patent application Ser. No. 10/149,352, filed on Jun. 10, 2002 now U.S. Pat. No. 7,173,122, for Antisense Oligonucleotide, and claims priority from PCT/GB00/04741, filed Dec. 12, 2000, and from British Application No. 9929487.8, filed Dec. 15, 1999.

SEQUENCE LISTING

The sequence information required by MPEP 2422.05 is identical to the sequence information provided in U.S. patent application Ser. No. 10/149,352, filed on Jun. 10, 2002 identified above.

The present invention relates to antisense oligonucleotides and their use in inhibiting expression of type I procollagen.

The collagens are a family of closely related proteins, with a triple helix protein structure. Numerous collagen types have been identified (>10) of which type I procollagen (consisting of two alpha1 chains and one alpha2 chain) is the principal component of bone, skin, and tendon. It has been recognized for many years that many pathological conditions are caused by overproduction of collagen fibers in the form of scars and excess fibrous tissues. For example, liver cirrhosis is a two-step process in which normal liver tissue is first destroyed by a virus or by alcohol and other toxins, and then excessive amounts of collagen fibers replace the damaged cells before normal liver cell regeneration. Idiopathic pulmonary fibrosis ("IPF") is a lethal condition in which normal lung tissue is gradually replaced by excessive amounts of collagen fibers. Progressive systemic sclerosis (Scleroderma) is a frequently lethal disease where skin and many internal organs become leather-like because of excessive depositions of collagen fibers. In many individuals, wounds or surgical incisions in the skin are followed by excessive depositions of collagen in the form of hypertrophic scars and keloids that present cosmetic problems and sometimes more serious consequences. Also, excessive scarring frequently occurs in normal individuals following trauma and surgical procedures. In these and related conditions, a means of specifically inhibiting collagen synthesis and deposition would be tremendous benefit. PCT Patent Application Publication No. WO 94/11494 discloses a DNA or RNA oligonucleotide comprising from 5 to 200 nucleotides substantially complementary to a mutant collagen nucleotide sequence or normal wild type collagen nucleotide sequence which is capable of inhibiting collagen gene expression. Preferred oligonucleotides are said to be antisense oligonucleotides. The Examples of WO 94/11494 describe a series of DNA oligonucleotides, some of which are antisense, that were synthesized primarily with regard to the region at the 3' end of exon 1 (from nucleotides 198 to 222) and the first two nucleotides of intron 1 of the gene for the proα1 chains of type I procollagen (COL1A1). The synthesized oligonucleotides were found to vary considerably in their ability of inhibit expression of an internally deleted mutant COL1A1 gene of human origin. The effectiveness of the oligonucleotides in inhibiting the expression of the human wild type COL1A1 gene was not however demonstrated. Since the structure and conformation of the RNA, transcripts of the human, mutant and wild type COL1A1 genes would most likely differ, it would not necessarily follow that oligonucleotides which are effective inhibitors of the expression of the mutant COL1A1 gene would also be effective inhibitors of the expression of the wild type COL1A1 gene. It would be desirable to identify antisense DNA oligonucleotides that are capable of inhibiting the expression of a wild type COL1A1 gene.

In accordance with the present invention, there is therefore provided an antisense DNA oligonucleotide comprising from 18 to 25 nucleotides which is complementary to a nucleotide sequence from position 750 to position 3000 inclusive of SEQ ID NO:1, wherein SEQ ID NO:1 comprises a nucleotide sequence encoding a polypeptide comprising an amino acid sequence according to SEQ ID No:2, the oligonucleotide being capable of inhibiting expression of the polypeptide in a cell that expresses it.

SEQ ID NO:1 is identical to the nucleotide sequence registered under EMBL accession no Z74615. SEQ ID NO:2 is the amino acid sequence of the polypeptide encoded by the nucleotide sequence of SEQ ID NO:1. The polypeptide encoded by SEQ ID NO:1 is a precursor of the wild type, proα1 chain of type I procollagen ("prepro-alpha1 (I) collagen").

The antisense DNA oligonucleotide according to the invention comprises 18, 19, 20, 21, 22, 23, 24 or 25 nucleotides and is preferably 20 nucleotides in length.

The antisense DNA oligonucleotide is preferably complementary to a nucleotide sequence in one of the following regions of SEQ ID NO:1, Region 1—from position 750 to position 900 inclusive,
Region 2—from position 1200 to position 1300 inclusive,
Region 3—from position 1400 to position 1500 inclusive,
Region 4—from position 1450 to position 1550 inclusive,
Region 5—from position 1850 to position 2000 inclusive,
Region 6—from position 2500 to position 2600 inclusive,
Region 7—from position 2850 to position 2950 inclusive,
Region 8—from position 2800 to position 3900 inclusive.

Particularly preferred antisense DNA oligonucleotides are those which are complementary to a nucleotide sequence in Region 2, 4, 6 or 8 of SEQ ID NO:1

The oligonucleotides of the invention may be prepared by any suitable method known in the art. The oligonucleotides are very conveniently prepared by synthetic chemical methods, for example, phosphoramidite chemistry by sulfurization with tetraethylthiuram disulfide in acetonitrile as described in *Tetrahedron Lett.*, 1991, 32, 30005-30008.

The oligonucleotides of the present invention are advantageous in that they inhibit expression of the wild type COL1A1 gene. They are therefore useful in the treatment or prevention of conditions/disorders caused by overproduction of collagen fibers, for example, liver cirrhosis, kidney, liver and heart fibrosis, scleroderma, hypertrophic scars and keloids. Accordingly, the present invention provides an antisense DNA oligonucleotide according to the invention for the use in therapy.

In another aspect, the invention provides the use of an antisense DNA oligonucleotide according to the invention in the manufacture of a medicament for use in therapy.

In the context of the present specification, the term "therapy" also includes "prophylaxis" unless there are specific indications to the contrary. The terms "therapeutic" and "therapeutically" should be construed accordingly.

The invention further provides a method of treating, or reducing the risk of, a collagen disorder in a patient suffering from, or at risk of, the disorder, which comprises administering to the patient a therapeutically effective amount of an antisense DNA oligonucleotide according to the invention.

For the above-mentioned therapeutic uses the dosage administered will, of course, vary with the oligonucleotide employed, the mode of administration, the treatment desired and the disorder indicated. Effective dosages are those which are able to inhibit collagen protein production in cells at a level which eliminates or reduces the symptoms or conditions associated with the collagen protein production.

The oligonucleotides according to the invention will generally be administered in the form of a pharmaceutical composition in which the oligonucleotide is formulated with a pharmaceutically acceptable adjuvant, diluent or carrier.

Thus, the present invention also provides a pharmaceutical composition comprising an antisense DNA oligonucleotide according to the invention in association with a pharmaceutically acceptable adjuvant, diluent or carrier.

The invention further provides a process for the preparation of a pharmaceutical composition of the invention which comprises mixing the antisense DNA oligonucleotide with a pharmaceutically acceptable adjuvant, diluent or carrier.

The pharmaceutical compositor of the invention may be administered topically in the form of, for example, a creme, lotion or ointment, or systemically, e.g. by oral administration in the form of tablets, capsules, syrups, powders or granules, or by parenteral administration in the form of sterile solutions or suspensions.

The invention also contemplates inhalation therapy for human patients either, or are at risk of having Pulmonary Fibrosis using a therapeutically effective dosage of the antisense DNA oligonucleotides, in a pharmaceutically acceptable adjuvant, diluent or carrier. Such adjuvants, diluents, and carriers are well known for use in inhalation therapy, and include various gases, vapors, powders, aerosols, and liquids. As but two examples, the antisense DNA oligonucleotides can be delivered to the patient's lungs through the use of various inhalers, which deliver the pharmaceutic composition according to the invention as an aerosol spray, and in addition, a nebulizer that delivers the pharmaceutical composition as a fine mist through a face mask.

In administering inhalation therapy according to the present invention to a patient having, or are at risk of having pulmonary fibrosis, the therapeutically effective dosage will vary considerably based upon several factors. Since the disease is universally lethal, unless reversed, and based upon the underlying cause of the scarring and thickening of the lung tissue, and because the duration of the disease varies in the particular patient, as well as the age and general health of the patient, and the volume of the lung or lungs involved, the dosage will vary, along with the timing of repeat dosages, depending upon the response of the patient to the treatment.

Although by definition, a disease characterized as being idiopathic means that the cause of the disease is unknown, a biopsy of the fibrous lung tissue can sometimes determine the cause of the disease and the dosage for the therapy can be adjusted accordingly.

The present invention will now be further explained by reference to the following illustrative Examples.

EXAMPLES

Example 1

Oligonucleotide Synthesis

Phosphorothioate oligodeoxynucleotides synthesis was carried out in a 1 μm scale on PE Biosystems 394 DNA synthesizer using phosphoramidite chemistry with TETD/acetonitrile sulphurizing reagent. Oligonucleotides were purified on Poly-Pak™ II cartridges (Glen Research), desalted on NAP™ 10 columns (American Pharmacia Biotech AB) and ion-exchanged using Dowex 50WX8-100 ion exchange resin (Aldrich). Twelve antisense DNA oligonucleotides (ASOs) were prepared having the following sequences (5'→3'):

| 1.  | GGACGACCAGGTTTTCCAGC | (SEQ ID NO: 3)  |
| --- | -------------------- | --------------- |
| 2.  | GCAGCACCAGCAGGGCCAGG | (SEQ ID NO: 4)  |
| 3.  | GCCAGGAGCACCAGGTTCAC | (SEQ ID NO: 5)  |
| 4.  | CTTCCTCTCCAGCAGGGCCA | (SEQ ID NO: 6)  |
| 5.  | GCCTTGCCGGGCTCTCCAGC | (SEQ ID NO: 7)  |
| 6.  | CGGGAACACCTCGCTCTCCA | (SEQ ID NO: 8)  |
| 7.  | GCAGGACCGACAGCGCCAGG | (SEQ ID NO: 9)  |
| 8.  | TCCATCTTTGCCAGCAGGAC | (SEQ ID NO: 10) |
| 9.  | CGTCCCTGAGCTCCAGCCTC | (SEQ ID NO: 11) |
| 10. | TTGGCCGTCAGCACCAGGG  | (SEQ ID NO: 12) |
| 11. | TTTCTCGCCAGCAGGGCCAG | (SEQ ID NO: 13) |
| 12. | CTCGATCTGCTGGCTCAGGC | (SEQ ID NO: 14) |

Example 2

Treatment of Cells

The human cell line WI-26 was grown in Dulbecco's modified Eagle's medium (DMEM) containing 10% fetal calf serum. The cells were plated in 48-well plates (Costar, Corning Inc.) to obtain 70-80% confluence. After 24 hours, the cells were washed two times with pre-warmed DMEM and 0.35 ml (for 48-well experiments) or 1 ml (6-well experiments) DMEM containing 5 μg/ml lipofection (Gibco BRL) or 2.5 μg/ml cytofectin GSV (Glen Research Ltd) and oligonucleotides at 200 nM were added to each well. After 4-5 hours at 37° C. the cells were washed two times with pre-warmed DMEM and 0.35 ml DMEM (48-well plates) or 1 ml DMEM (6 well plates) was added together with ascorbic acid at 10 μg/ml. The cells were incubated for 20 hours prior to analysis of collagen levels.

Example 3

Protein Analysis

At the end of the experiment, 150 μl of medium was removed and the amount of secreted type I procollagen determined using an ELISA kit (AmershamPharmacia Ltd) and the results expressed as nanograms of procollagen in the medium/10,000 cells. To correct for cell numbers, plates were washed with pre-warmed PBS, cells treated with trypsin and cell numbers determined using a automated Coulter counter. For 6-well experiments, the cells were counted, treated with 1 ml TRI reagent (SIGMA Ltd) and proteins and RNA extracted according to the manufacturers guidelines. The protein pellet was re-suspended in 1% SDS containing protease inhibitors. 30-100 μgs cellular proteins were heated at 100° C. for 5 minutes and then lectrophoresed in a 4-12% SDS polyacrylamide gel. Proteins were electrophoretically transferred to nitrocellulose filters and hybridized with an antibody against a synthetic peptide corresponding to human proα(I)

chain of type 1 collagen (obtained from Dr. Larry Fisher, NIH, USA). The proα1(1) band was detected using ECL (Pierce Ltd). Protein loading was determined by treating the membrane with an antibody to GAPDH (Advanced Immunochemicals). Protein loading was normalized to GAPDH levels using desitometry.

Example 4

RNA Analysis

RNA was extracted using TRI reagent and the final pellet was re-suspended in 0.5% SDS. One to three micrograms of total RNA were electrophoresed in a formaldehyde denaturing gel according to standard procedures (Sambrook, J., Fritsch, E. F. and Maniatis, T. (1989) Molecular Cloning: A Laboratory Manual, $2^{nd}$ Ed., Cold Spring Harbor Laboratory Press, (Amersham) and hybridized for 24 hours to an alpha1 (1) cDNA probe radiolabeled using a T7 polymerase kit (AmershamPharmacia). Following washing, the filter was exposed to X-ray film and the film developed 4-24 hours later. The autoradiographic images of the alpha1(1) transcripts (4.8 kb & 5.8 kb) were analyzed by densitometric analysis and RNA loading was corrected using the intensity of the GAPDH transcript or the intensity of the 28S rRNA as internal controls.

Results

Table I below shows the average percentage (%) collagen inhibition which related to either collagen levels in the medium or collagen mRNA levels. In the treated cell assay used, there was a very good correlation between percentage collagen inhibition as measured in the medium and percentage inhibition of intracellular collagen mRNA levels.

TABLE I

| ASO | AVERAGE % COLLAGEN INHIBITION |
|---|---|
| CGACGACCAGGTTTTCCAGC (SEQ ID NO: 3) | 50 |
| GCAGCACCAGCACCAGGTTCAC (SEQ ID NO: 4) | 50-80 |
| GCCAGGAGCACCAGGTTCAC (SEQ ID NO: 5) | 50 |
| CTTCCTCTCCAGCAGGGCCA (SEQ ID NO: 6) | 50-60 |
| GCCTTGCGGGCTCC TCCAGC (SEQ ID NO: 7) | 50 |
| CGGGAACACCTCGCTCTCCA (SEQ ID NO: 8) | 50 |
| GCAGGACCGACAGCGCCAGG (SEQ ID NO: 9) | 50 |
| TCCATCTTTGCCAGCAGGAC (SEQ ID NO: 10) | 50 |
| GGTCCCTGAGCTCCAGCCTC (SEQ ID NO: 11) | 50 |
| TTGGCCGTCAGCACCAGGG (SEQ ID NO: 12) | 50-80 |
| TTTCTCGCCAGCAGGGCCAG (SEQ ID NO: 13) | 50-70 |
| CTCGATCTGCTGGCTCAGGC (SEQ ID NO: 14) | 50-80 |

It is, of course, known in the treatment of cancer patients, to administer various chemotherapy drugs with the primary intent to kill or otherwise interfere with the growth of the cancer cells, but which all too often have very severe side effects, not the least of which involve impaired lung function, typically resulting in pulmonary fibrosis.

While there are many drugs used in chemotherapy, the drugs identified as bleomycine, cyclophosphamide and methotrexate, amongst others, are generally known to cause pulmonary fibrosis, especially in middle age men and women, and without regard to sexual, racial or geographical predilection.

Because of being known to cause pulmonary fibrosis, patients having a history of impaired lung function, especially having any history of pulmonary fibrosis, are generally considered as not being good candidates for chemotherapy involving either bleomycin, cyclophosphomide or methotrexate, or similar such drugs.

In a case where there is apparently no presence of pulmonary fibrosis, and chemotherapy involving one of these herein identified is commenced, pulmonary fibrosis is oftentimes induced, causing the cancerous tumor to be enveloped in an abnormal formation of fibre-like scar tissue surrounding the cancerous tumor. This fibrous tissue envelope creates a barrier which prevents, or at least inhibits the chemotherapy drugs from continuing to move inside the tumor. In short, this barrier inhibits the ability of the drug to address the malignant cells of the tumor.

The present invention provides a solution for addressing this pulmonary fibrosis problem by treating the patient with the antisense DNA oligonucleotide contemplated by this present invention, contemporaneously with chemotherapy treatment involving drugs such as bleomycin, cyclophosphamide and methotrexate which can otherwise cause pulmonary fibrosis.

Because the use of bleomycin as a chemotherapy drug has become so common, i.e., it is often the drug of choice in attacking several types of cancer, such as squamous cell carcinoma of the head and neck, penis, cervix and vulva, lymphomas and testicular cancer, malignant pleural effusion, bone cancer, Kaposi's Sareoma, Malignant Melanoma, Mycosis Fungoides and thyroid cancer its use is described in greater detail hereinafter.

Bleomycin was initially marketed in the U.S. by Bristol-Myers Squibb, through its precursor Bristol Laboratories, under the brand name Blenoxane. Bristol-Myers Squibb currently still supplies Blenoxane. Generic versions of bleomycin are currently available from Bedford, Sicor and Mayne Pharma.

Bleomycin acts by induction of DNA strand breaks. Some studies suggest that bleomycin also inhibits incorporation of thymidine into DNA strands. Bleomycin is a metal-chelating molecule that is also thought to produce superoxide and hyroxide free radicals, through action as a pseudoenzyme, which also damages the DNA.

In chemotherapy, the drug is typically administered:
as an infusion (drip) into the vein through a cannula (a fine tube inserted into the vein). It may be given through a central line, which is inserted under the skin into a vein near the collarbone, or through a PICC line, which is inserted into a vein in the crook of the arm.
by injection into a muscle (intramuscular injection)
by injection through a chest drain after drainage of a pleural effusion. This can help to seal the two layers of the pleura together to stop a pleural effusion from recurring.

If the patient already has some degree of pulmonary fibrosis, either ideopathic or from a known cause, it will most likely be more effective to begin treatment by first administering the antisense DNA oligonucleotides contemplated by this invention to treat the patient for the existing pulmonary fibrosis. After some period of time, for example, days or weeks later, depending upon the severity of the pulmonary fibrosis, the chemotherapy treatment using the bleomycin can begin.

If there is no existing pulmonary fibrosis, the bleomycin and the antisense DNA oligonucleotides can be administered together, at the same time, or spaced shortly apart if necessary for whatever the reason.

The antisense DNA oligonucleotides can be administered in accordance with the invention, by infusion (drip) into a vein, by inhalation therapy as discussed at length herein, by spraying or pouring such antisense DNA oligonucleotides directly over the exterior surface of the tumor being treated, or by injection into muscle tissue, by injection into tissue surrounding the tumor, or by injection into the tumor itself, or by any other known method for introducing the antisense DNA oligonucleotides into the malignant tumor. Without limiting the forgoing, the invention fully contemplates mixing the chemotherapy drug with the antisense DNA oligonucleotides together and administering the mixture to the patient using each or all of the methods discussed above to administer the drugs when done separately.

The invention claimed is:

1. A method of treating a malignant tumor in a patient and of treating, or reducing the risk of, a collagen disorder in such patient suffering from, or at risk of, a lung disease relating to the collagen disorder, which comprises:

administering therapy to the patient using a therapeutically effective amount of an antisense DNA oligonucleotide which is selected from SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13 and SEQ ID NO:14, or combinations thereof; and administering to the patient at least one chemotherapy drug which itself has a propensity for causing such lung disease.

2. The method according to claim 1, wherein the antisense DNA oligonucleotide comprises from 19 to 20 nucleotides which is complementary to a nucleotide sequence from position 750 to position 3900 inclusive of SEQ ID NO:1, wherein SEQ ID NO:1 comprises a nucleotide sequence encoding a polypeptide comprising an amino acid sequence according to SEQ ID NO:2; the oligonucleotide being capable of inhibiting expression of the polypeptide in a cell that expresses it.

3. The method according to claim 2, wherein the antisense DNA oligonucleotide is complementary to a nucleotide sequence from position 750 to position 900 inclusive of SEQ ID NO:1.

4. The method according to claim 2, wherein the antisense DNA oligonucleotide is complementary to a nucleotide sequence from position 1200 to position 1300 inclusive of SEQ ID NO:1.

5. The method according to claim 2, wherein the antisense DNA oligonucleotide is complementary to a nucleotide sequence from position 1400 to position 1500 inclusive of SEQ ID NO:1.

6. The method according to claim 2, wherein the antisense DNA oligonucleotide is complementary to a nucleotide sequence from position 1450 to position 1550 inclusive of SEQ ID NO:1.

7. The method according to claim 2, wherein the antisense DNA oligonucleotide is complementary to a nucleotide sequence from position 1850 to position 2000 inclusive of SEQ ID NO:1.

8. The method according to claim 2, wherein the antisense DNA oligonucleotide is complementary to a nucleotide sequence from position 2500 to position 2600 inclusive of SEQ ID NO:1.

9. The method according to claim 2, wherein the antisense DNA oligonucleotide is complementary to a nucleotide sequence from position 2850 to position 2950 inclusive of SEQ ID NO:1.

10. The method according to claim 2, wherein the antisense DNA oligonucleotide is complementary to a nucleotide sequence from position 3800 to position 3900 inclusive of SEQ ID NO:1.

11. The method according to any of claims 1-10, wherein said oligonucleotide is administered in association with a pharmaceutically acceptable adjuvant, diluent, or carrier.

12. The method according to claim 1, wherein said chemotherapy drug comprises bleomycin.

13. The method according to claim 1, wherein said chemotherapy drug comprises cyclophosphomide.

14. The method according to claim 1, wherein said chemotherapy drug comprises methotrexate.

15. The method according to claim 1, wherein said antisense DNA oligonucleotides, and said chemotherapy drug are mixed together before being administered to the patient.

16. The method according to claim 1, wherein said antisense DNA oligonucleotides and said chemotherapy drug are administered simultaneously to the patent without being mixed outside the patient's body.

17. The method according to claim 1, wherein said antisense DNA oligonucleotides and said chemotherapy drug are administered to the patient using inhalation therapy involving the antisense DNA oligonucleotides and/or the chemotherapy drug.

18. The method according to claim 1, wherein said antisense DNA oligonucleotides and said chemotherapy drug are administered to the patient using an infusion into one or more veins of the patient involving the antisense DNA oligonucleotides and/or the chemotherapy drug.

19. The method according to claim 1, wherein said antisense DNA oligonucleotides and said chemotherapy drug are administered to the patient involving the antisense DNA oligonucleotides and/or the chemotherapy drug being injected into the patient's tissue external to a malignant tumor.

20. The method according to claim 1, wherein said antisense DNA oligonucleotides and said chemotherapy drug are administered to the patient involving the antisense DNA oligonucleotides and/or the chemotherapy drug being injected into the patient's malignant tumor.

21. The method according to claim 1, wherein said antisense DNA oligonucleotides and said chemotherapy drug are administered to the patient involving the antisense DNA oligonucleotides and/or the chemotherapy drug being injected into muscle tissue in said patient.

22. The method according to claim 1, wherein said antisense DNA oligonucleotides and said chemotherapy drug are administered to the patient involving the antisense DNA oligonucleotides and/or the chemotherapy drug being applied directly to the exterior surface of a malignant tumor.

23. The method according to claim 1, wherein said antisense DNA oligonucleotides and said chemotherapy drug are administered to the patient involving the antisense DNA oligonucleotides and/or the chemotherapy drug being injected through a chest drain in the patient following the drainage of a pleural effusion.

* * * * *